(12) United States Patent
Takahashi et al.

(10) Patent No.: US 8,389,959 B2
(45) Date of Patent: Mar. 5, 2013

(54) FLUORESCENCE ANALYZING DEVICE AND FLUORESCENCE ANALYZING METHOD

(75) Inventors: Satoshi Takahashi, Hitachinaka (JP); Tsuyoshi Sonehara, Kokubunji (JP); Tomoyuki Sakai, Kokubunji (JP); Takanobu Haga, Kokubunji (JP); Hirokazu Kato, Mito (JP); Nobutaka Kumazaki, Hitachinaka (JP); Takuya Matsui, Mito (JP)

(73) Assignee: Hitachi High-Technologies Corp., Tokyo (JP)

( * ) Notice: Subject to any disclaimer, the term of this patent is extended or adjusted under 35 U.S.C. 154(b) by 37 days.

(21) Appl. No.: 13/147,147

(22) PCT Filed: Nov. 30, 2009

(86) PCT No.: PCT/JP2009/006456
§ 371 (c)(1),
(2), (4) Date: Jul. 29, 2011

(87) PCT Pub. No.: WO2010/086935
PCT Pub. Date: Aug. 5, 2010

(65) Prior Publication Data
US 2011/0284768 A1  Nov. 24, 2011

(30) Foreign Application Priority Data

Jan. 30, 2009  (JP) .................................. 2009-018952

(51) Int. Cl.
*G01N 21/64* (2006.01)
(52) U.S. Cl. ................................... 250/459.1
(58) Field of Classification Search ................ 250/459.1
See application file for complete search history.

(56) References Cited

U.S. PATENT DOCUMENTS

| | | |
|---|---|---|
| 6,917,726 B2 | 7/2005 | Levene et al. |
| 2004/0029152 A1 | 2/2004 | Ishida |
| 2005/0024636 A1 | 2/2005 | Nakamura |
| 2006/0231400 A1 | 10/2006 | Inaba et al. |

FOREIGN PATENT DOCUMENTS

| | | |
|---|---|---|
| JP | 09-257813 | 10/1997 |
| JP | 10-068694 | 3/1998 |

(Continued)

OTHER PUBLICATIONS

Taliani et al., "Laser-Excited fluorescence from dibenzofuran in a biphenyl host," 1984, Journal of Physical Chemistry, vol. 88, pp. 2357-2360.*

(Continued)

*Primary Examiner* — Kiho Kim
(74) *Attorney, Agent, or Firm* — McDermott Will & Emery LLP

(57) ABSTRACT

The present invention has an object to provide a method for efficiently detecting an image with a smaller number of pixels.

The invention relates to fluorescence analysis which uses a substrate having a plurality of regions for being capable of immobilizing biologically-related molecules in positions of lattice points of a lattice structure, and which causes the fluorescence from a certain lattice point to be wavelength-dispersed in a direction other than the direction toward the adjacent closest lattice point. According to an embodiment, for example, the number of pixels of a two-dimensional sensor required for fluorescence analysis of the regions with the biologically-related molecules immobilized can be set to several hundred times to fifty times smaller than that in the conventional case without degrading the measurement accuracy. This can achieve the improvement of throughput, reduction in price, and/or improvement of the operability of an analyzing device.

20 Claims, 9 Drawing Sheets

FOREIGN PATENT DOCUMENTS

| | | |
|---|---|---|
| JP | 2002-214142 | 7/2002 |
| JP | 2004-271337 | 9/2004 |
| JP | 2005-070031 | 3/2005 |
| JP | 2006-292368 | 10/2006 |

OTHER PUBLICATIONS

Takashi Funatsu et al., "Imaging of single fluorescent molecules and individuals ATP turnovers by single myosin molecules in aqueous solution,"Letters to Nature, vol. 374, pp. 555-559 (1995).

Ido Braslaysky et al., "Sequence information can be obtained from single DNA molecules," Proc. Natl. Acad. Sci. USA, vol. 100, No. 7, pp. 3960, 2003.

M.J. Levene et al., "Zero-Mode Waveguides for Single-Molecule Analysis at High Concentrations," Science 2003, vol. 299, pp. 682-686.

Hameer Ruparel et al., " Design and synthesis of a 3'-O-allyl photocleavable fluorescent nucleotide as a reversible terminator for DNA sequencing by synthesis," Proc. Natl. Sci. USA, vol. 102, pp. 5932, 2005.

* cited by examiner

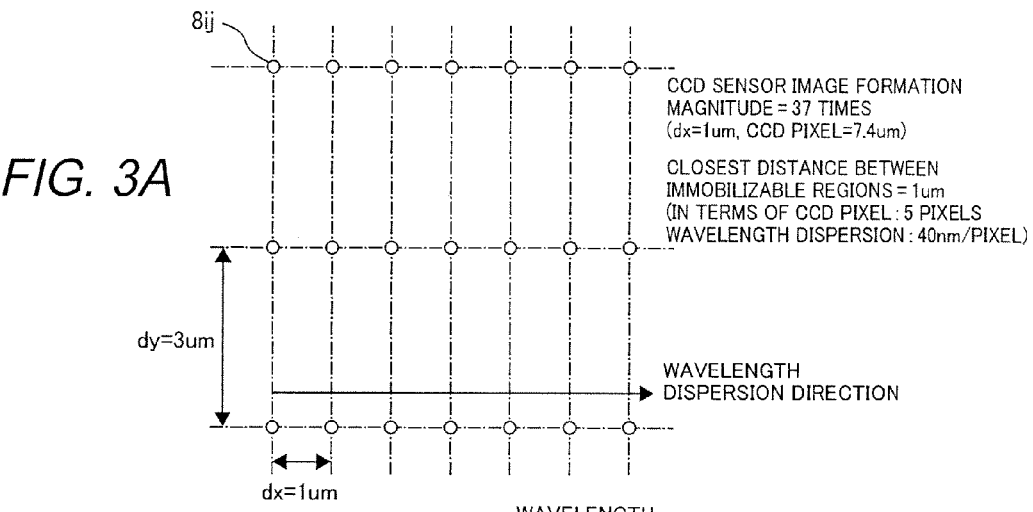
FIG. 3A
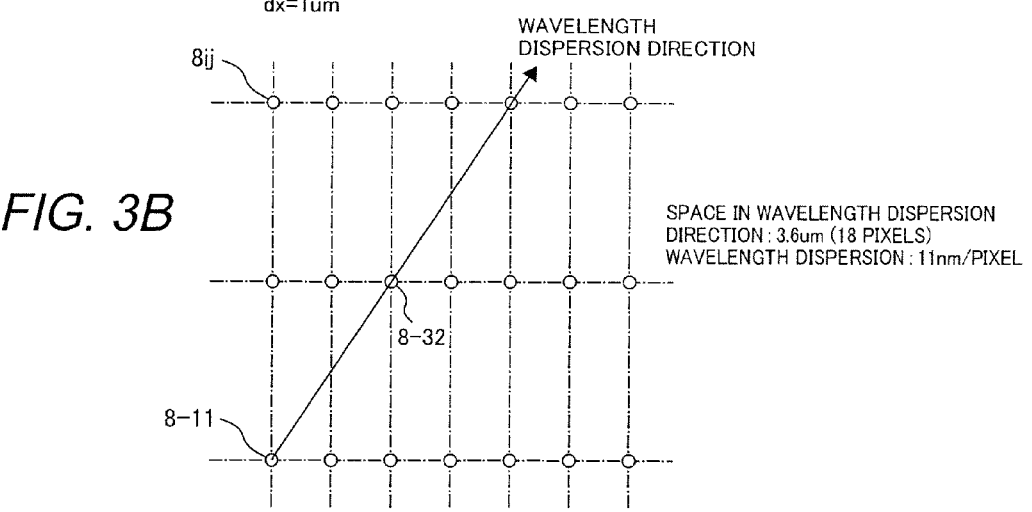
FIG. 3B
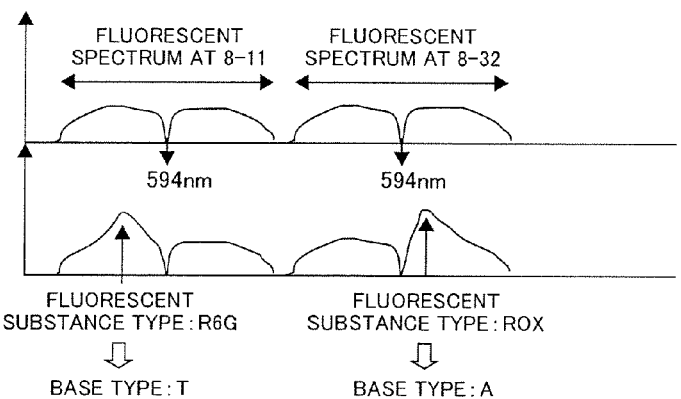
FIG. 3C
FIG. 3D

FIG. 5

EXAMPLE OF LATTICE STRUCTURE

| | dy=1um | dy=2um | dy=3um |
|---|---|---|---|
| dx=1um | (lattice pattern) | (lattice pattern) | (lattice pattern) |
| WAVELENGTH DISPERSION DIRECTION AND DISPERSION POWER | DISPERSION DIRECTION: 45 DEGREES, DISPERSION: 11nm/PIXEL | DISPERSION DIRECTION: 63.4 DEGREES, DISPERSION: 7.1nm/PIXEL | DISPERSION DIRECTION: 71.6 DEGREES, DISPERSION: 5.1nm/PIXEL |
| | DISPERSION DIRECTION: 26.6 DEGREES, DISPERSION: 7.1nm/PIXEL | DISPERSION DIRECTION: 45 DEGREES, DISPERSION: 5.7nm/PIXEL | DISPERSION DIRECTION: 56.3 DEGREES, DISPERSION: 4.4nm/PIXEL |
| | DISPERSION DIRECTION: 18.4 DEGREES, DISPERSION: 5.1nm/PIXEL | DISPERSION DIRECTION: 33.7 DEGREES, DISPERSION: 4.4nm/PIXEL | DISPERSION DIRECTION: 45 DEGREES, DISPERSION: 3.8nm/PIXEL |
| | | DISPERSION DIRECTION: 76 DEGREES, DISPERSION: 3.9nm/PIXEL | DISPERSION DIRECTION: 38.9 DEGREES, DISPERSION: 5.1nm/PIXEL |
| | | | DISPERSION DIRECTION: 80.5 DEGREES, DISPERSION: 2.6nm/PIXEL |

CCD SENSOR IMAGE FORMATION MAGNITUDE = 37 TIMES
(CCD PIXEL SIZE = 7.4um, WHEN DISPERSING AND MAKING IMAGE OF FLUORESCENCE AT POSITION OF SUBSTANCE AT RATE OF 1um SPACING IN FIVE PIXELS)

CCD SENSOR IMAGE FORMATION MAGNITUDE = 37 TIMES
(CCD PIXEL SIZE = 7.4um, WHEN DISPERSING AND MAKING IMAGE OF FLUORESCENCE
AT POSITION OF SUBSTANCE AT RATE OF 1um SPACING IN FIVE PIXELS)

FLUORESCENCE ANALYZING DEVICE AND FLUORESCENCE ANALYZING METHOD

RELATED APPLICATIONS

This application is the U.S. National Phase under 35 U.S.C. §371 of International Application No. PCT/JP2009/006456, filed on Nov. 30, 2009, which in turn claims the benefit of Japanese Application No. 2009-018952, filed on Jan. 30, 2009, the disclosures of which applications are incorporated by reference herein.

TECHNICAL FIELD

The present invention relates to photometric analysis devices, and more particularly, to a device for performing photometric analysis by applying light to biologically-related molecules, for example, DNA, RNA, or protein.

BACKGROUND ART

Methods have been conventionally proposed for observing the shape of an object disposed on the surface of a substrate by irradiating the object with an excitation light. For example, in a device disclosed in Patent Document 1, an evanescent wave is generated on the surface of a transparent substrate by irradiating the substrate with an excitation light output from an excitation light source and causing the total reflection of the excitation light therein. Then, a scattered light of the evanescent wave generated by a specimen on the substrate is detected. The device disclosed in Patent Document 1 does not disperse the scattered light.

For example, Patent Document 2 discloses a device for dispersing a fluorescence and a scattered light emitted from a specimen component excited by an evanescent wave. In the device disclosed in Patent Document 2, the specimen component is not immobilized on an interface of a flow path.

On the other hand, a device is proposed which is designed to immobilize a plurality of biomolecules on the surface of a substrate, and to generate an evanescent wave in a certain range of the substrate surface like Patent Document 1 to thereby make an image of light emission from the biomolecules excited by the evanescent wave. Non-fluorescent biomolecules are immobilized on the substrate, and a reaction solution containing fluorescent molecules is made to flow onto the substrate, whereby the fluorescence generated from the position where the biomolecules are immobilized is observed. This can observe a bonding reaction between the biomolecules and the molecules in the reaction solution. For example, first, an unlabeled single-stranded DNA is immobilized on the substrate, into which a reaction solution is introduced. The reaction solution contains fluorescence labeled bases which are labeled by different fluorescent substances according to the type of the base. The fluorescence generated from the position of immobilizing the molecule is dispersed, while bonding a complementary base to the single-stranded DNA, so that the sequence of the immobilized DNA can be determined.

Recently, as disclosed in Non-Patent Document 2, methods are proposed for determining the sequence of bases of the DNA by immobilizing the DNA on a substrate. The molecules of specimen DNA fragments to be analyzed are captured on the substrate one by one in a random manner, and each molecule is extended substantially by one base. The result is detected by measuring the fluorescence to thereby determine the sequence of bases. Specifically, four types of dNTP derivatives (MdNTP) with detectable labels are captured into a template DNA as a substrate of a DNA polymerase, and then can terminate a DNA chain elongation reaction under the presence of a protective group. In a step of a DNA polymerase reaction, the DNA polymerase reaction is performed by using these four types of dNTP derivatives. Then, in a step of detection, the captured MdNTP is detected by fluorescence or the like. In a step of returning, the MdNTP is returned to a state of being extendable. These steps are set as one cycle and repeatedly performed, so that the sequence of bases of the specimen DNA is determined. Since in this technique the base sequence of the DNA fragments can be determined by each molecule, a number of fragments can be simultaneously analyzed, which can increase the throughput for analysis. Since in this system the base sequence can be determined for each single DNA molecule, cloning which was a problem of the related art, and the purification and amplification of the specimen DNA at a PCR or the like possibly become unnecessary, so that the acceleration of genomic analysis or genetic diagnosis can be expected. This method immobilizes the specimen DNA fragment molecules to be analyzed on the substrate surface in a random manner, and thus needs an expensive camera with the number of pixels which is several hundreds times larger than the number of the captured DNA fragment molecules. That is, when a distance between the DNA fragment molecules is adjusted to an average of 1 micron, some DNA fragment molecules have a distance therebetween more than the average, and other DNA fragment molecules have a distance therebetween less than the average. In order to detect the DNA molecules by separation of them, it is necessary to detect fluorescent images at narrower intervals in terms of a substrate surface. Normally, the images are required to be measured at intervals of one several tenth of the distance.

On the other hand, Non-Patent Document 3 and Patent Document 3 employ a nano-opening evanescent illumination detecting system which can further reduce a volume of irradiation of an excitation light rather than in a total reflection evanescent illumination detecting system to thereby improve the sensitivity of detection of the fluorescence. Two glass substrates, namely, a glass substrate A and a glass substrate B are disposed in parallel. A plate-like aluminum thin film of about 100 nm in thickness with a nano-sized opening of 50 nm in diameter is deposited on one side of the glass substrate opposed to the glass substrate B. The aluminum thin film needs to have an optical-shielding characteristic. A reaction chamber is provided in an intermediate position between the two glass substrates, and a solution is charged into the reaction chamber, whereby a solution layer is formed between the two glass substrates. The reaction chamber has an inlet and an outlet for the solution. The solution is charged from the inlet and discharged from the outlet, so that the solution can flow in parallel to the glass substrates and the aluminum thin film. Thus, the composition of the solution of the solution layer can be changed to an arbitrary one. When the excitation light having a wavelength of 488 nm and generated from an Ar ion laser is applied vertically to the glass substrate A by stopping down the aperture of an objective lens in the direction opposite to the glass substrate B, an evanescent field of the excitation light is formed in the solution layer near the bottom plane of the inside of the nano-sized opening. Thus, the excitation light is not transferred anymore to the further inside of the solution layer. In contrast, the emission of fluorescence is detected by forming an image on a two-dimensional CCD using the objective lens. The intensity of excitation light in the evanescent field is attenuated in an exponential manner with increasing distance from the bottom plane of the nano-sized opening. The intensity of excitation light becomes one tenth (1/10) at a distance of about 30 nm from the bottom plane of the nano-sized opening. Further, in the nano-opening evanescent illumination detecting system, unlike the total reflection evanescent illumination detecting method, the width of irradiation of the excitation light in the parallel to the glass substrate is limited to the diameter of the opening, namely, 50 nm, which further reduces the volume of irradiation of the excitation light. Thus, the fluorescent emitted from a free fluorescent substance and a background light including Raman scattering of water can be drastically reduced. As a result, under the presence of the free fluorescent substances at a higher concentration, only the fluorescent substances marked in biomolecules of interest can be selectively detected, which can achieve the detection of fluorescence with very high sensitivity.

In the invention, the above fluorescence detecting system can be applied to measurement of the captured dNTP in the elongation reaction of the DNA molecule. In the same manner as the term "specimen component immobilized surface", the plane where the evanescent field is generated can be referred to as an "evanescent field interface surface".

RELATED ART TECHNICAL DOCUMENTS

Patent Documents

Patent Document 1:
  Japanese Unexamined Patent Publication No. 1997(Hei 09)-257813
Patent Document 2:
  Japanese Unexamined Patent Publication No. 2005-70031
Patent Document 3:
  U.S. Pat. No. 6,917,726
Patent Document 4
  Japanese Unexamined Patent Publication No. 2002-214142

Non-Patent Documents

Non-Patent Document 1: Nature Vol. 374, 555-559 (1995)
Non-Patent Document 2: Proc. Natl. Acad. Sci. USA, vol. 100, pp 3960, 2003
Non-Patent Document 3: SCIENCE 2003, Vol. 299, pp. 682-686
Non-Patent Document 4: Proc. Natl. Acad. Sci. USA, vol. 102, pp 5932, 2005

SUMMARY OF INVENTION

Technical Problem

The inventors of the present application have been dedicated themselves to studying fluorescence analysis using an evanescent field, and as a result have found the following.

In a device for analyzing biomolecules by making an image of fluorescence from the biomolecules immobilized on a substrate surface, the different kinds of biomolecules are generally immobilized on regions (spots) individually fixed on the substrate, and the fluorescence generated from each spot is separated and detected by making an image thereof. In order to analyze many kinds of biomolecules as much as possible for a short time, and to reduce the amount of a reagent consumed, the spots are preferably disposed on the substrate as densely as possible in a range that can be optically dispersed. Further, in order to reduce the amount of reagent consumed per spot, the number of biomolecules immobilized within one spot is preferably as small as possible. Ideally, only one molecule exists in one spot. As described in Non-Patent Document 1, a fluorescence detecting method has the sensitivity that can detect even one molecule. However, in order to obtain a good S/N ratio by dispersing and detecting the fluorescence from a few molecules, a spectroscopic imaging method with less loss is preferable. Thus, a dispersive spectroscopic imaging method using a dispersion element, such as a prism or a diffraction grating, or a method for obtaining images using a plurality of image sensors by dispersing the fluorescence with a dichroic mirror (dichroic/multi sensor spectroscopic imaging method) is preferable.

The spots are preferably disposed on the substrate as densely as possible in the range that can be optically dispersed. However, a dichroic/multi sensor spectroscopic imaging method needs image sensors, the number of which is the same as that of fluorescent labeled substances to be used, which leads to increase in cost of a detector. Since the fluorescent image is split by a dichroic mirror or the like, the S/N ratio is not necessarily large. A dispersive spectroscopy imaging method has a merit that the use of the minimum image sensors (for example, only one image sensor) enables the detection. However, when the distance between the spots becomes narrower, the fluorescent image provided by wavelength-dispersion of fluorescence generated from the spot would be overlapped on another fluorescent image of an adjacent spot. In order to improve the detection accuracy of fluorescence, a distance between the spots with biomolecules immobilized on the substrate has to be widened, which makes it difficult to provide the spots densely.

When the biomolecules are immobilized on the substrate in a random manner, the necessary number of pixels is several hundred times more than the number of spots on the substrate, which reduces the speed of detection and needs an expensive two-dimensional sensor. Further, since the fluorescent image has to be detected at high resolution, a condenser lens having a large numerical aperture NA needs to be used, which makes the system more expensive.

The present invention has an object to provide a method for efficiently detecting an image with the smaller number of pixels. For example, the invention relates to the method which can efficiently perform detection with the smaller number of pixels when detecting a fluorescent image generated from DNA fragment molecules immobilized on the substrate by the two-dimensional sensor. Further, for example, the invention relates to the detection method at low cost and/or with good operability when detecting the fluorescent image from the DNA fragment molecules immobilized and captured on the substance by the two-dimensional sensor.

Solution to Problem

The invention is directed to fluorescence analysis which uses a substance with a plurality of regions for being capable of immobilizing biologically-related molecules in the positions of lattice points of a lattice structure to thereby cause fluorescence generated from a certain lattice point to be wavelength-dispersed in a direction other than the direction toward the adjacent closest lattice point.

Effects of Invention

According to embodiments, the number of pixels of the two-dimensional sensor required for fluorescence analysis of the regions where the biologically-related molecules can be immobilized can be reduced to one several tenth to one fiftieth of that of the conventional case without degrading the measurement accuracy. This arrangement can achieve improvement of the throughput, reduction in price, and/or improvement of the operability of the analyzing device.

BRIEF DESCRIPTION OF DRAWINGS

FIG. 3 is an explanatory diagram of a system for detecting a fluorescence from the substrate by wavelength-dispersion in a second embodiment;

FIG. 5 is a conceptual diagram of lattice structures of a substrate and dispersion directions in a third embodiment;

DESCRIPTION OF EMBODIMENTS

Figure 1:
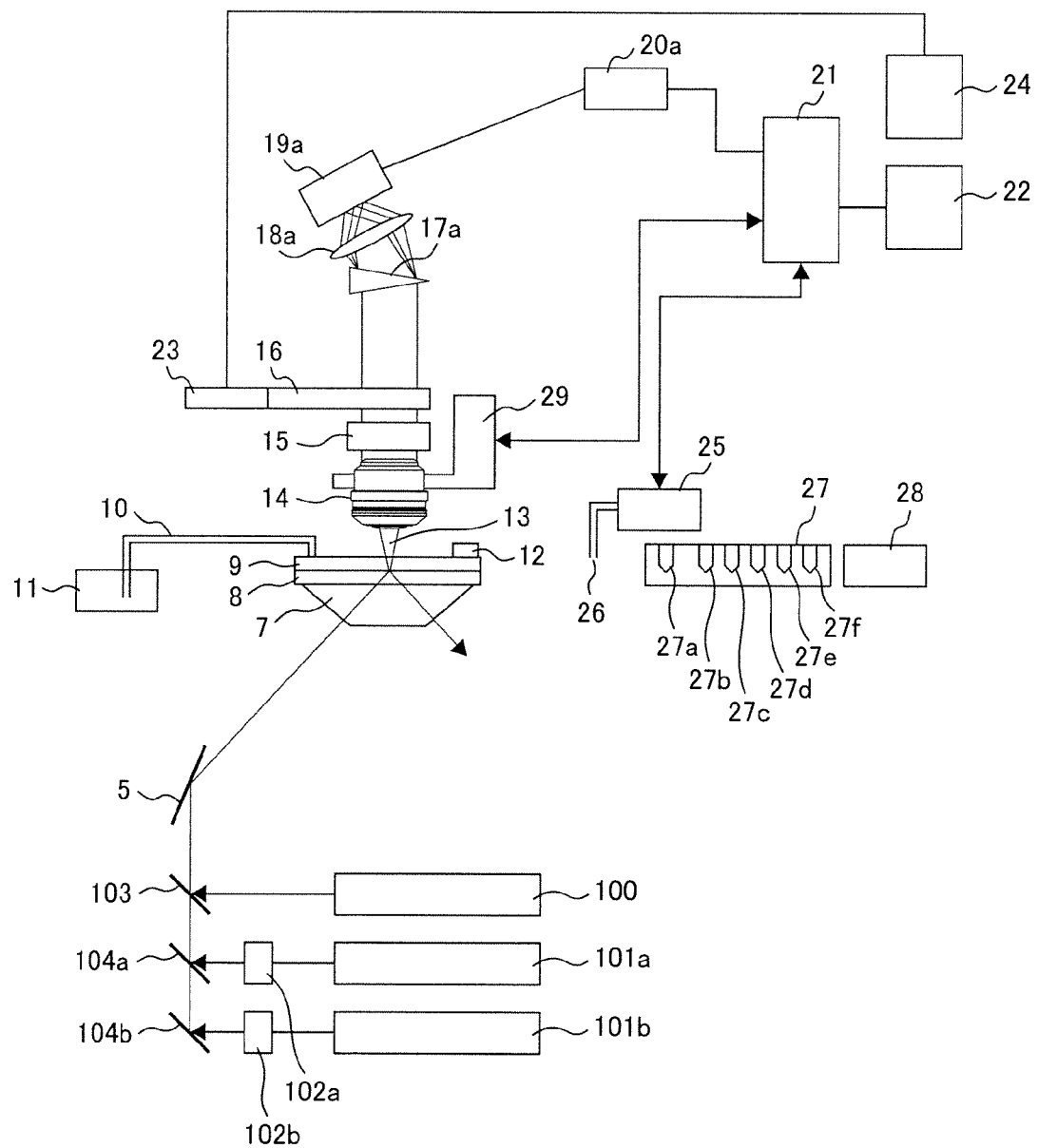
FIG. 1 is a configuration diagram of a DNA detection device using a fluorescence analysis method in a first embodiment.

In the embodiments, a plurality of objects to be measured are positioned with high accuracy, and an image of each object to be measured is formed at a certain pixel of a detector with a plurality of detection pixels.

Preferably, an excitation light for measurement of fluorescence is applied to a substrate with oligonucleotide or the like immobilized thereon, and the generated fluorescences are collected. Then, the collected light is dispersed, whereby an image of the light is made on a two-dimensional sensor so as to detect the fluorescence by the sensor. In this method, the substrate is provided with a plurality of regions for immobilizing the oligonucleotide or the like. These regions are arranged on the substrate in the form of lattice points of a lattice structure. The fluorescence generated from the certain lattice point is wavelength-dispersed in a direction other than the direction toward the adjacent closest lattice point, and the intensity of fluorescence at each wavelength dispersed is measured.

Preferably, the fluorescence generated from the certain lattice point is wavelength-dispersed in the direction at an angle of +10 to +170 degrees, or at an angle of −10 to −170 degrees with respect to the angle from the certain lattice point toward the adjacent closest lattice point, which is referred to as a "wavelength dispersion direction". The intensity of the dispersed fluorescence image is measured at each wavelength.

Further, preferably, the fluorescence generated from the certain lattice point is wavelength-dispersed in the direction from the certain lattice point toward an adjacent arbitrary lattice point which is the second or higher-order closest from the certain lattice point. This direction is referred to as a "wavelength dispersion direction". The intensity of the dispersed fluorescence is measured at each wavelength.

The above lattice structure contains a two-dimensional rectangular lattice or triangle lattice, and the like.

A plurality of regions individually immobilized on the substrate are provided. In order to arrange the regions on the substrate in the form of the lattice points of the lattice structure, a metal structure is provided on the surface of the substrate. The metal structure contains fine particles made of metal, such as gold, chrome, silver, or aluminum, a metal structure having a size equal to or smaller than the wavelength of the excitation light, for example, a structure whose part has fine protrusions, or a thin film or the like with fine openings. For the metal structure, biomolecules are immobilized to the surface of the metal structure. In this case, the spatial position of the metal structure can be detected and used as a reference marker for the position by detecting photoluminescence and/or light scattering of the structure. In the case of the metal thin film with fine openings, biomolecules are immobilized in the openings. In this case, the spatial position of the metal structure can be detected and used as the reference marker for the position by detecting a Raman scattered light of a specimen solution around biomolecules, or photoluminescence or light scattering of the metal structure near the biomolecules.

The biomolecules, such as oligonucleotide, are preferably immobilized on all lattice points, but may be in at least two lattice points.

A distance from the certain lattice point to the adjacent closest lattice point is preferably in a range of 100 nm to 10000 nm, and more preferably in a range of 500 nm to 2000 nm.

The region (spot, or region at the lattice point) with oligonucleotide immobilized thereon preferably has a diameter of 100 nm or less, which is preferably equal to or less than at least one third of the distance between the adjacent closest lattice points.

Preferably, a film-like material having an optical shielding function is effectively formed at the reaction regions on the substrate surface other than the regions with the oligonucleotide immobilized thereon, by vapor deposition of a metal film or the like.

The substrate preferably has at least two markers for positioning.

A spectroscopic portion is preferably comprised of at least one dispersion element. The dispersion element uses a prism, such as a wedge prism, or a diffraction grating.

A processor preferably calculates a difference between a first image detected when biomolecules do not emit light, and a second image detected when biomolecules emit light. By comparing the difference with the first image, the type of the biomolecule emitting light is determined.

Preferably, the sensor detects the light emitted from the biomolecules which is overlapped on light emitted from the structure. The processor may form positional information using the light overlapped as a background light. The processor determines the type of the biomolecule based on a relative position of a brighter part than its surroundings in the overlapped light.

The present embodiment discloses a fluorescence analyzing device which includes a substrate where biologically-related molecules are immobilized, and which is adapted to irradiate the substrate with light for measurement of fluorescence, to disperse a generated fluorescence, and to measure the dispersed fluorescence by a two-dimensional sensor. A plurality of regions where the biologically-related molecules can be immobilized are provided in positions of lattice points of a lattice structure at the substrate. A fluorescence generated from a certain lattice point is wavelength-dispersed in a direction other than a direction toward the adjacent closest lattice point.

Further, another embodiment discloses a fluorescence analyzing method which includes the steps of irradiating a substrate where biologically-related molecules are immobilized, with light for measurement of fluorescence; dispersing a generated fluorescence; and measuring the dispersed fluorescence by a two-dimensional sensor. A plurality of regions where the biologically-related molecules can be immobilized are provided in positions of lattice points of a lattice structure at the substrate, and a fluorescence generated from a certain lattice point is wavelength-dispersed in a direction other than the direction toward the adjacent closest lattice point.

Moreover, in another embodiment, the fluorescence generated from the certain lattice point is wavelength-dispersed in the direction at an angle of +10 to +170 degrees, or −10 to −170 degrees with respect to the angle from the lattice point toward the adjacent closest lattice point.

In another embodiment, the fluorescence generated from the certain lattice point is wavelength-dispersed in the direction toward an adjacent arbitrary lattice point which is the second or higher-order closest from the certain lattice point.

In another embodiment, the lattice structure is a two-dimensional longitudinal lattice structure.

In another embodiment, the lattice structure is a triangle lattice structure.

In another embodiment, a metal fine structure is provided in the position of the lattice point of the lattice structure.

Further, in another embodiment, the metal fine structure is comprised of fine particles made of gold, chrome, silver, or aluminum.

Moreover, in another embodiment, the metal fine structure is a structure whose part has fine protrusions.

In another embodiment, the metal fine structure is a metal structure having a size equal to or less than a wavelength of an excitation light.

In another embodiment, the substrate is used which has fine openings located in the positions of the lattice points of the lattice structure, and which is formed of an optically opaque thin film.

Further, in another embodiment, biologically-related molecules are immobilized on the surface of the metal structure or the bottom of the opening.

In another embodiment, a prism is optically bonded to the substrate, or a part of the substrate has a prism-like shape. The light for measurement of fluorescence is applied to the substrate via the prism, so that the light is totally reflected by the surface of the substrate to thereby form an evanescent field.

In another embodiment, an optically transparent elastic material is sandwiched between the substrate and the prism, so that the substrate is optically bonded to the prism. The light for measurement of fluorescence is totally reflected by the surface of the substrate to thereby form the evanescent field.

In another embodiment, a distance between the lattice points is in a range of 100 nm to 10000 nm.

In another embodiment, the region where the biologically-related molecule can be immobilized has a diameter of 100 nm or less.

In another embodiment, the fluorescence is dispersed at a wavelength in a range of 500 nm to 700 nm.

In another embodiment, the fluorescence is separated into components in at least two wavelength bands, which are individually wavelength-dispersed.

Further, in another embodiment, the fluorescence is separated into components in two wavelength bands, which are individually wavelength-dispersed within the maximum bandwidth of 100 nm, and detected by two two-dimensional sensors.

The new features and effects of the present invention will be described below with reference to the accompanying drawings. The drawings are used to understand the invention itself, and do not limit the claims. Respective embodiments can be appropriately combined.

First Embodiment

This embodiment will describe below a device and method for determining a base sequence. In the device and method, molecules of a specimen DNA fragment to be analyzed are captured one by one on the surface of a substrate at equal intervals, and are extended substantially by one base, so that each fluorescent labeled molecule captured is detected to determine the base sequence. Specifically, four types of dNTP derivatives with detectable labels are captured into a template DNA as a substrate of a DNA polymerase and can terminate a DNA chain elongation reaction under the presence of a protective group. In a step of a DNA polymerase reaction, the DNA polymerase reaction is performed by using these four types of dNTP derivatives. Then, in a step of detection, the captured dNTP derivative is detected based on fluorescence or the like. In a step of returning, the dNTP derivative is returned to a state of being extendable. These steps are set as one cycle and repeatedly performed, whereby the sequence of bases of the specimen DNA is determined. The present operation is based on a monomolecular fluorescent detecting method in which the measurement is performed in an environment like a clean room via a HEPA filter.

[Device Structure]

FIG. 1 is a configuration diagram of a DNA detection device using a fluorescence analysis method in this embodiment. The device has the structure similar to that of a microscope, and is designed to measure the state of elongation of the DNA molecules captured on a substrate 8 by detection of fluorescence.

Figure 2A:
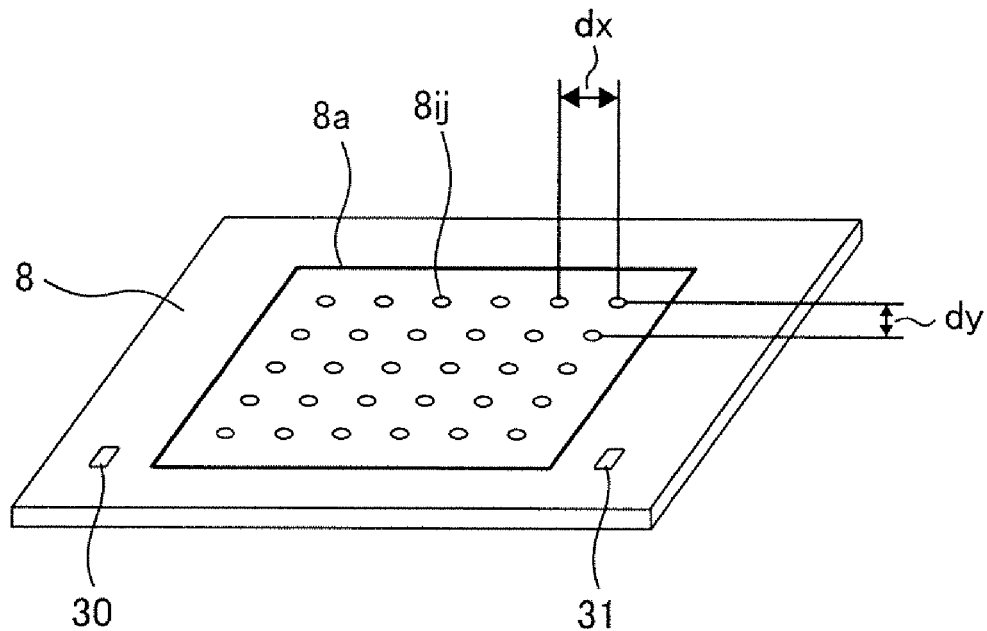
FIG. 2 is a configuration diagram of a substrate in the first embodiment.
Figure 2B:
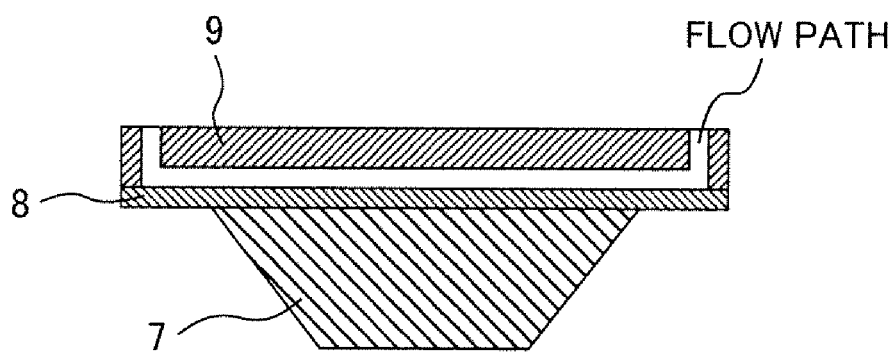

The substrate 8 has the structure shown in FIG. 2. The substrate 8 has at least a part thereof made of a transparent material, for example, synthetic crystal. The substrate 8 has a reaction region 8a which is made of transparent material, and is brought into contact with a reagent or the like. A plurality of regions 8ij with the DNA immobilized are formed within the reaction region 8a. Each region 8ij has a diameter of 100 nm or less. The region is subjected to a surface treatment for capturing the DNA. The surface treatment involves, for example, bonding streptavidin to the substrate, and reacting the substrate with a biotin labeled DNA fragment to thereby capture the DNA. Alternatively, oligonucleotide containing poly T is immobilized, and one end of the DNA fragment is tagged with poly A, so that the DNA can be captured by a hybridization reaction. At this time, the concentration of the DNA fragment is appropriately adjusted, so that only a monomolecular DNA can be captured by the individual region 8ij. By reducing the size of the region 8ij, the number of molecules in the region can be set to one. Since then, the substrate in this state is measured. Such substrates include a substrate having every region 8ij with the monomolecular DNA immobilized thereon, and a substrate having the regions 8ij whose parts have the DNA immobilized thereon. When the parts of the regions 8ij have the DNA immobilized thereon, the DNA is not immobilized on the remaining regions 8ij, which are vacant. The distance dx between the regions 8ij is set to 1 micrometer, and the distance dy therebetween is set to 3 micrometers. In this way, the regions 8ij form a lattice structure (two-dimensional longitudinal lattice structure), and thus are located in the positions of the lattice points. Such a substrate with the regions positioned at equal intervals is formed, for example, by the way disclosed in Japanese Unexamined Patent Publication No. 2002-214142. Each of the distances dx and dy is larger than the size of each region 8ij, and preferably equal to or less than about 4000 nm. The reaction region 8a of the substrate is set to have a size of 1 mm×1 mm.

The reaction region 8ij can be larger than the above size. Alternatively, the reaction regions, each having a size of 0.5 mm×0.5 mm, may be arranged side by side in one- or two-dimensional manner at certain intervals. A metal structure may be disposed in the region 8ij. The metal structure can also be formed by a semiconductor process, which can use electron beam lithography, dry etching, wet etching, or the like. The metal structure is made of gold, copper, aluminum, chrome, or the like, and has a size equal to or less than a wavelength of an excitation light. The metal structure in use can be a rectangular parallelepiped, a circular cone, a cylinder, a structure whose part is protruded, or the like.

Various types of fluorescent substances can be used as a fluorescent label for the dNTP. For example, Bodipy-FL-510, R6G(trademark), ROX(trademark), and Bodipy-650(trademark) are used. The Bodipy-FL-510 is a fluorescent dye having a maximum fluorescence wavelength of about 510 nm. The R6G is a fluorescent dye having a maximum fluorescence wavelength of about 555 nm. The ROX is a fluorescent dye having a maximum fluorescence wavelength of about 605 nm. The Bodipy-FL-650 is a fluorescent dye having a maximum fluorescence wavelength of about 650 nm. By being labeled with these different four fluorescent substances, four kinds of dNTPs whose 3' ends are labeled with an ally group (3'-O-allyl-dGTP-PC-Bodipy-FL-510, 3'-O-allyl-dTTP-PC-R6G, 3'-O-allyl-dATP-PC-ROX, 3'-O-allyl-dCTP-PC-Bodipy-650) are used.

A laser beam from a laser light source 101a for excitation of fluorescence (Ar laser, 488 nm: for excitation of Bodipy-FL-510, and R6G) passes through λ/4 (quarter-) wave plate 102a to be converted into a circular polarized light. A laser beam from a laser light source 101b for excitation of fluorescence (He—Ne laser, 594.1 nm: for excitation of ROX and Bodipy-650) passes through a λ/4 (quarter-) wave plate 102b to be converted into a circular polarized light. Both laser beams are overlapped on each other via a mirror 104b and a dichroic mirror 104a (which reflects the light having a wavelength of 520 nm or less). The overlapped light vertically enters an incidence plane of a prism 7 made of crystal for total reflection illumination via a mirror 5 as shown in the figure, and is applied from the back side of the substrate 8 with the DNA molecules immobilized thereon. The quartz prism 7 and the substrate 8 are in contact with each other via a matching oil (nonfluorescent glycerine or the like). The laser beam does not reflect at an interface between the prism and the substrate, and is guided into the substrate 8. The substrate 8 has its surface covered with a reaction solution (water). At an interface between the substrate surface and the solution, the laser beam totally reflects to become evanescent illumination. Thus, the measurement of fluorescence can be performed at a high S/N ratio.

Near the substrate, a temperature adjustment device is disposed, but the illustration thereof will be omitted in the drawing. For normal observation, halogen illumination can be applied from under the prism, which is omitted in the drawing.

A laser light source 100 (YAG laser, 355 nm) other than the laser light sources 101a and 101b is disposed. A laser beam therefrom can be overlapped with the laser beams from the laser light sources 101a and 101b via a dichroic mirror 103 (which reflects the light having a wavelength of 400 nm or less) to be applied on the same optical axis. This laser is used in the step of returning the dNTP derivative to a state of being extendable after detecting the fluorescence of the captured dNTP derivative.

A reagent or the like is made to flow over the upper part of the substrate 8 to configure a flow chamber 9 for reaction. The flow chamber has an inlet 12, a dispensing unit 25 with a dispensing nozzle 26, a reagent storage unit 27, and a chip box 28, and is designed to dispense the reagent of interest. In the reagent storage unit 27, a specimen solution container 27a, dNTP derivative solution containers 27b, 27c, 27d, and 27e (note that the containers 27c, 27d, and 27e are for a backup), and a washing liquid container 27f are disposed. A dispersing chip in the chip box 28 is attached to the dispensing nozzle 26, which sucks an appropriate reagent solution, and then guides the reagent solution from the chamber inlet to the reaction regions of the substrate to cause a reaction. A waste liquid is discharged into a waste liquid container 11 via a waste liquid tube 10. These are automatically performed by a control PC 21.

The flow chamber is formed of a transparent material in the optical axis, and in the chamber, the fluorescence detection is performed. Fluorescences 13 are collected by a condenser lens (objective lens) 14 controlled by an automatic focusing device 29. The fluorescence having a necessary wavelength is taken out and the light having an unnecessary wavelength is removed by a filter unit 15. The fluorescence is dispersed by a wavelength dispersion prism 17a, and an image of the fluorescence is made and detected on a two-dimensional sensor camera 19a (high sensitivity cooling CCD camera) by an imaging lens 18a. The control of setting of an exposure time of the camera, of timing of capturing a fluorescent image, and the like is performed by a control PC 21 via a two-dimensional sensor camera controller 20a. The filter unit 15 uses two types of notch filters (for 488 nm and 594 nm) for removal of the light having a laser beam wavelength, and a bandpass interference filter (in a transmittance bandwidth of 510 to 700 nm) for permitting the detected fluorescence at the wavelength to penetrate therethrough.

This system includes a unit or a lens tube 16 for observation of transmitted light, a TV camera 23, and a monitor 24 for adjustment or the like, and thus can observe the state of the substrate 8 in real time by illumination of halogen or the like.

The optical axis is inclined by the wavelength dispersion prism 17a, but a plurality of prisms with different dispersion levels can be combined not to incline the optical axis.

As shown in FIG. 2, positioning markers 30 and 31 are inscribed on the substrate 8. The markers 30 and 31 are disposed in parallel to the regions 8ij, and a distance between the marker and the region is defined. By detecting the markers by observation with transmission illumination, the positions of the regions 8ij can be calculated.

The two-dimensional sensor camera used in this embodiment is a CCD area sensor. Specifically, this embodiment uses a cooling CCD camera having a pixel size of 7.4 micrometers×7.4 micrometers, and in which the number of pixels is 2048×2048. In addition to the CCD area sensor, an imaging camera, such as a C-MOS area sensor, can be used as the two-dimensional sensor camera. Further, CCD area sensors are categorized into a backside illumination type and a front illumination type in terms of structure, both of which can be used. Further, an electron multiplication type CCD camera having a multiplication function of a signal inside an element is effectively used in order to achieve high sensitivity. The sensor is preferably of a cool type, and can reduce dark noise from the sensor to thereby enhance the accuracy of measurement by being cooled down to about −20° C. or less.

The fluorescent image from the reaction region 8a may be detected at one time, or can be divided into some parts. In this case, a X-Y moving mechanism for moving the position of the substrate is disposed under a stage, whereby the control PC controls the moving to an irradiation position, the irradiation of light, and the detection of a fluorescent image. In this embodiment, the X-Y moving mechanism is not illustrated.

[Reaction Steps]

Steps of a stepwise elongation reaction will be described below. The reaction steps are performed with reference to "Proc. Natl. Acad. Sci. USA, vol. 100, pp 3960, 2003 (Non-Patent Document 2)", and "Proc. Natl. Acad. Sci. USA, vol. 102, pp 5932, 2005(Non-Patent Document 4)". A buffer with streptavidin added thereto is introduced from the inlet 12 into the chamber, and the streptavidin is bonded with biotin immobilized on the metal structure to form a biotin-avidin complex. A primer is hybridized to a single-stranded DNA template which is a biotin-labeled target. The DNA template-primer complex and the buffer with excessive amount of biotin added thereto are introduced into the chamber, so that the above monomolecular DNA template-primer complex is immobilized on the metal structure disposed on each lattice point via the biotin-avidin bonding. After the immobilizing reaction, the excessive DNA template-primer complexes and biotin are washed from the chamber with a buffer for washing. Thermo Sequenase Reaction buffer is produced by adding Thermo Sequenase polymerase to four kinds of dNTPs (3'-O-allyl-dGTP-PC-Bodipy-FL-510, 3'-O-allyl-dTTP-PC-R6G, 3'-O-allyl-dATP-PC-ROX, 3'-O-allyl-dCTP-PC-Bodipy-650) which are labeled with the respective different four kinds of fluorescent substances and whose 3' ends are labeled with an allyl group. The Thermo Sequenase Reaction buffer obtained is introduced into the chamber from the inlet 12 to cause an elongation reaction. The dNTP captured in the DNA template-primer complex has its 3' end labeled with the allyl group, whereby one or more bases are not captured in the DNA template-primer complex. After the elongation reaction, unreacted various kinds of dNTPs and polymerase are washed by the buffer for washing. Then, a chip is irradiated with laser beams generated from an Ar laser light source 101a and a He—Ne laser light source 101b at the same time. The irradiation of the chip with the laser beam excites the fluorescent substance labeling the dNTP captured in the DNA template-primer complex, so that the fluorescence generated from the fluorescent substance is detected. The type of the base of the dNTP can be determined by determining the wavelength of the fluorescence from the fluorescent substance for labeling the dNTP captured in the DNA template-primer complex. Since this case corresponds to an evanescent illumination, only an area near the surface of the reaction region becomes an excitation light irradiation area, so that measurement can be performed with less background light without exciting the fluorescent substance existing in a region other than the surface. Although in the above case, the washing is performed after the elongation reaction, the measurement can be performed without washing when the concentration of the fluorescent labeled dNTP is small.

Then, the laser beam generated from the YAG laser light source 100 is applied to the chip to remove the fluorescent substance labeling the dNTP captured in the complex by optical cutting. Then, a solution containing palladium is introduced into a flow path. The allyl group at the 3' end of the dNTP derivative captured in the complex is transformed to a hydroxyl group in a palladium catalytic reaction. By transforming the allyl group at the 3' end to the hydroxyl group, the elongation reaction of the DNA template-primer complex can be restarted. After the catalytic reaction, the chamber is washed by the buffer for washing. This is repeatedly performed to determine the sequence of the immobilized single-stranded DNA template.

This system can simultaneously measure fluorescences from the regions 8*ij* of the reaction region 8*a*. When different DNA templates are immobilized on the regions 8*ij*, the types of bases of the dNTPs captured in the different DNA template-primer complexes, that is, the sequences of the DNA templates can be simultaneously determined.

[Detection of Dispersed Image of Fluorescence]

FIG. 3 is an explanatory diagram showing a system for detecting a fluorescence at the substrate by wavelength-dispersing the fluorescence. FIG. 3A is a schematic diagram of a part of the surface of the substrate 8 having the regions 8*ij* (lattice points) formed thereon for immobilizing the DNA. The magnification of image formation on a CCD camera is 37 times, and the distance dx of 1 µm (dx=1 µm) is divided into five parts to be detected by CCD pixels. The distance between the closest lattice points is 1 µm. Dispersion of the fluorescence in that direction gives the dispersion of 40 nm per pixel, which makes it difficult to discriminate between four types of fluorescent substances in a range of 500 nm to 700 nm.

As shown in FIG. 3B, when the fluorescence is dispersed in the direction not toward the closest lattice point, but toward an adjacent point (8-32 shown in the figure) at the third closest distance from the certain point, the distance between the lattice points is 3.6 µm, giving the dispersion of 11 nm per pixel. Thus, the fluorescences from the four types of fluorescent substances in the range of 500 nm to 700 nm can be discriminated.

FIG. 3C shows fluorescent emission spectra obtained when the metal nanostructure is formed on each of the regions 8*ij* (lattice points) for immobilizing the DNA and the fluorescence is dispersed in the direction shown in FIG. 3B. As shown in the figure, the spectra from the lattice points 8-11 and 8-32 are detected. It is known that luminescence is generated from the metal nanostructure. The spectra in the figure indicate such luminescence. Each spectrum has a part whose intensity drastically becomes small at the midway thereof. This is because the fluorescence is cut by a 594 nm notch filter in a filter unit 15. The position of the valley-like part is analyzed and marked, so that a wavelength axis of the fluorescence from each lattice point can be configured.

FIG. 3D shows fluorescent spectra obtained after the elongation reaction of each dNTP, in which peaks based on the fluorescences of the fluorescent substances are observed. Based on the reference point of 594 nm, the fluorescent peak can be calculated to determine the type of the fluorescent substance. In the figure, the types of fluorescent substances are R6G and ROX, which correspond to T and A as the type of base, respectively.

As mentioned above, according to this embodiment, in the system based on the dispersive spectroscopy imaging method, the fluorescence generated from the certain lattice point is dispersed in the wavelength dispersion direction at an angle toward an adjacent arbitrary lattice point which is the second or higher-order closest from the certain lattice point. The intensity of each dispersed fluorescence is measured at each wavelength, whereby the discrimination between the fluorescent substances can be performed with high accuracy. Further, the detection of photoluminescence from the metal structure can provide the wavelength reference at each reaction point of the substrate, whereby the discrimination between the types of fluorescence substances, which was difficult to achieve in the dispersive spectroscopy imaging method, can be performed with high accuracy in this embodiment. As a result, the determination of the base sequence can be performed with high accuracy.

The metal structure on the substrate surface can be formed of any one of chrome, silver, aluminum, and the like, in addition to gold. The wavelength reference can be obtained not only based on a center wavelength of the filter, but also based on a spectrum of scattered laser radiation or the like.

In this embodiment, the different dNTPs are labeled with four types of different fluorescent substances. However, the four types of dNTPs can be labeled with the same one type of fluorescent substance. In this case, only one type of laser light source for excitation is necessary. The reaction is performed in the order of A→C→G→T→A→C, etc.

The laser light vertically enters the quartz prism 7. For this reason, the substance and the prism can be integrally moved.

According to this embodiment, for example, the necessary number of pixels of the two-dimensional sensor for the regions with oligonucleotide immobilized thereon to be measured can be decreased to one several hundredth to one fiftieth of that of the conventional case without degrading the measurement accuracy, which enables the efficient detection. Thus, in use of the same two-dimensional sensor, the fluorescent images from more regions can be obtained at one time, which can achieve the high throughput. In use of the camera with the smaller number of pixels, the measurement can be performed at lower cost.

For example, when the number of regions with oligonucleotide immobilized thereon to be measured can be set to the same as that in the conventional system, this embodiment can efficiently detect the fluorescence with the smaller number of pixels, and thus can provide the two-dimensional sensor at low cost. Since an optical resolution of this system can be substantially set to a distance or spacing between the regions with oligonucleotide immobilized thereon, this embodiment cannot require a condenser lens having a large numerical aperture, can use a low-cost lens, and can improve the operability because an immersion lens does not need to be used.

Second Embodiment

Figure 4:
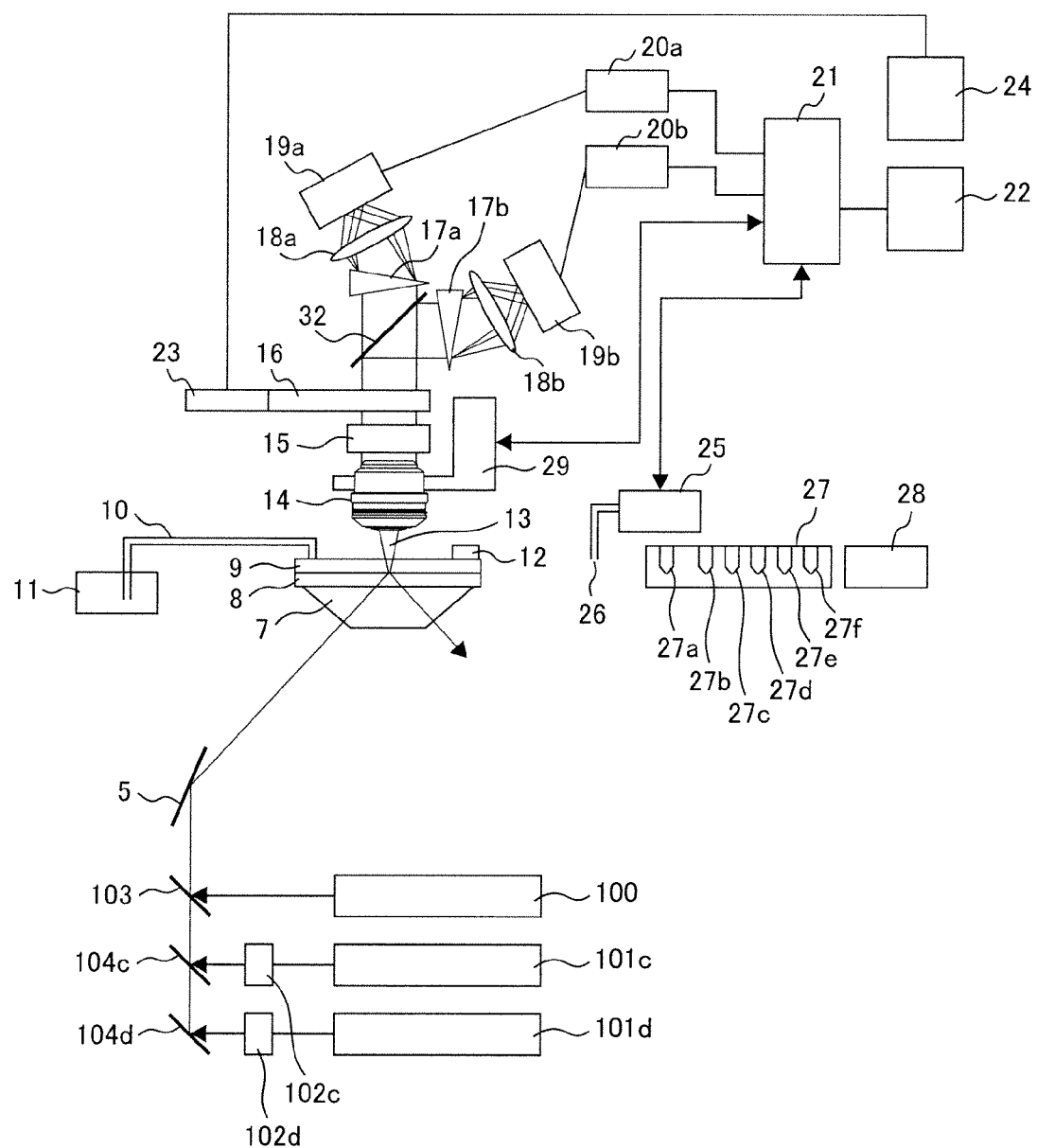
FIG. 4 is a configuration diagram of a DNA detection device in the second embodiment.

FIG. 4 shows the structure of this embodiment. In this embodiment, DNA sequencing is performed in a stepwise elongation reaction using four types of fluorescent substances. The structures of a chamber, a chip, and the like are the same as those of the first embodiment. Now, different points from the first embodiment will be mainly described below.

As a fluorescent label for the dNTP, Alexa Fluor 488(trademark), Cy3(trademark), Cy5(trademark), and Cy5.5(trademark) are used. The Alexa Fluor 488 is a fluorescent dye having a maximum fluorescence wavelength of about 520 nm. The Cy3 is a fluorescent dye having a maximum fluorescence wavelength of about 570 nm. The Cy5 is a fluorescent dye having a maximum fluorescence wavelength of about 670 nm. The Cy5.5 is a fluorescent dye having a maximum fluorescence wavelength of about 694 nm. Other various fluorescent substances can be used as the fluorescent substance. Four types of dNTPs labeled with one fluorescent substance can be used. A laser beam from a laser light source 101c for excitation of fluorescence (solid laser, 505 nm: for excitation of Alexa Fluor 488 and Cy3) passes through a λ/4 (quarter-) wave plate 102c to be converted into a circular polarized light. A laser beam from a laser light source 101d for excitation of fluorescence (semiconductor laser, 635 nm: for excitation of Cy5 and Cy5.5) passes through a λ/4 (quarter-) wave plate 102d to be converted into a circular polarized light. Both laser beams are overlapped on each other via a mirror 104d and a dichroic mirror 104c (which reflects the light having a wavelength of 520 nm or less). The overlapped light vertically enters an incidence plane of the prism 7 made of crystal for total reflection illumination via the mirror 5 as shown in the figure, and is applied from the back side of the substrate 8 with the DNA molecules immobilized thereon. The quartz prism 7 and the substrate 8 are in contact with each other via matching oil (nonfluorescent glycerine or the like). The laser beam does not reflect at an interface between the prism and the substrate, and is guided into the substrate 8. The substrate 8 has its surface covered with a reaction solution (water). At an interface between the substrate surface and the solution, the laser beam totally reflects to become evanescent illumination. Thus, the measurement of fluorescence can be performed at a high S/N ratio.

In this embodiment, the excitation wavelengths are 505 nm and 635 nm which are spaced apart from each other. When the dispersion is performed using the same wavelengh dispersion element, the fluorescence in the region which does not need to be dispersed (for example, having a wavelength in a range of 570 to 620 nm) is dispersed. The detection of the fluorescence in this wavelength band does not affect the result, and causes some pixels not to be used, so that the CCD cannot be used effectively. For this reason, fluorescences are collected by the condenser lens (objective lens) 14. The fluorescence having the necessary wavelength is taken out, and the light having an unnecessary wavelength is removed by the filter unit 15. Then, the fluorescence is separated into a fluorescence component for the Alexa Fluor 488 and Cy3, and a fluorescence component for the Cy5 and Cy5.5 by the dichroic mirror 32. The fluorescence components are dispersed by wavelength dispersion prisms 17a and 17b, and images thereof are made and detected on two-dimensional sensor cameras 19a and 19b (high-sensitivity cooling CCD camera) by imaging lenses 18a and 18b. The control of setting of an exposure time of the camera, of timing of capturing a fluorescent image, or the like is performed by the control PC 21 via two-dimensional sensor camera controllers 20a and 20b. The filter unit 15 uses two types of notch filters (for 505 nm and 635 to 642 nm) for removal of a laser beam, and a bandpass interference filter (in a transmission bandwidth of 510 to 700 nm) for permitting the fluorescence in the wavelength band for detection to penetrate therethrough. Thus, the two-dimensional sensor camera 19a can have a range of wavelength dispersion of 500 to 580 nm in order to detect the fluorescence component for the Alexa Fluor 488 and Cy3, whereas the two-dimensional sensor camera 19b can have a range of wavelength dispersion of 630 to 700 nm in order to detect the fluorescence component for the Cy5 and Cy5.5. Each dispersion can be performed in a relatively narrow range of wavelength, which can effectively activate the CCD pixels. In the first embodiment, the fluorescence having a wavelength of 500 to 700 nm, that is, within a bandwidth of 200 nm, is dispersed. However, in this embodiment, the fluorescence having a wavelength within a bandwidth of 80 nm is sufficiently dispersed. When using the substance with the same lattice structure, the fluorescent substances can be separated with higher accuracy.

A wavelength marker has its reference frame selected by adjusting a filter to detect a wavelength of the scattered laser beam, or from a spectrum of luminescence.

The sequencing will be described below according to an actual measurement procedure. A M13-DNA fragment is used as a model specimen. The end of the M13-DNA fragment is biotinylated in accordance with the normal method. The biotinylated DNA solution is held in a specimen solution container 27a shown in FIG. 4. A mixture solution (containing polymerase) of a caged dATP labeled with Alexa Fluor 488, a caged dCTP labeled with Cy3, a caged dGTP labeled with Cy5, and a caged dTTP labeled with Cy5.5 is held in a dNTP derivative solution container 27b. The labeled caged dNTP is a caged compound containing nucleotide with a 2-nitrobenzyl group, and is captured as a complementary strand. However, the activity that causes the labeled caged dNTP to be sequentially captured in a complementary synthesis reaction is suppressed. Thus, a DNA chain is extended by one base and then the elongation reaction is terminated. When an ultraviolet light having a wavelength of 360 nm or less is applied, the caged material (2-nitrobenzyl group) is liberated to enhance the inherent activity of the nucleotide, which can cause the synthesis of a next dNTP.

The biotinylated DNA template is introduced into a flow chamber by the dispensing unit 25 to be reacted with the substrate. After washing, an oligo primer is introduced thereinto, whereby the primer is hybridized onto the biotinylated DNA. Thus, an elongation reaction of a complementary strand is performed. First, after washing, a labeled caged dNTP solution is introduced. A base to be captured is determined according to a base of the template next to the primer bonding position. Laser beams from a laser light source 101*c* (505 nm) and a laser light source 101*d* (635 nm) are applied to the substrate, and the fluorescences are measured by the two-dimensional sensor cameras. In the same way as the first embodiment, the captured base can be determined according to the presence or absence of the fluorescence or depending on a difference in wavelength of the fluorescence. Then, a laser beam from a laser light source 100 (355 nm) is applied to return the activity of the dATP. The cycle of this procedure is repeatedly performed, whereby the base sequence can be determined.

This embodiment uses a fluorescent labeled caged dNTP as a reagent which can stop the DNA chain elongation reaction under the presence of a protective group by being captured in the DNA template as a substrate of the DNA polymerase. The fluorescent labeled caged dNTP is one of four types of dNTP derivatives with labels which can be detected, and which can be returned to the state of being extendable by any means. A dNTP derivative which is obtained by bonding a fluorescent substance with nucleotide via a disulfide bond can be applied in the same way. In this case, under the presence of fluorescent substance, the elongation is stopped, so that the disulfide bond can be chemically dissociated by a Tris[2-carboxyethyl]phosphine reagent and the like to return the dNTP derivative to the state of being extendable.

Third Embodiment

FIG. 5 shows a schematic diagram showing lattice structures of another substrate and dispersion directions. Different points from the first and second embodiments will be mainly described below.

FIG. 5 illustrates the dispersion direction at each lattice point and a wavelength dispersion bandwidth per pixel of the CCD in the case of each of longitudinal lattice structures having a distance dx=1 μm and a distance dy=1, 2, and 3 μm. This is a case in which an image of the fluorescence is made on the substrate at a rate of 1 μm spacing in five pixels of the CCD. The wavelength dispersion bandwidth varies depending on an image formation magnitude, or on the size of the dx and dy. In this embodiment, by setting the wavelength-dispersion direction in a direction other than the direction toward the adjacent closest lattice point, the range of wavelength per pixel can be increased without overlapping the fluorescence image on a fluorescence image from another lattice point, which can detect the intensity and wavelength of fluorescence with high accuracy.

Fourth Embodiment

Figure 6:
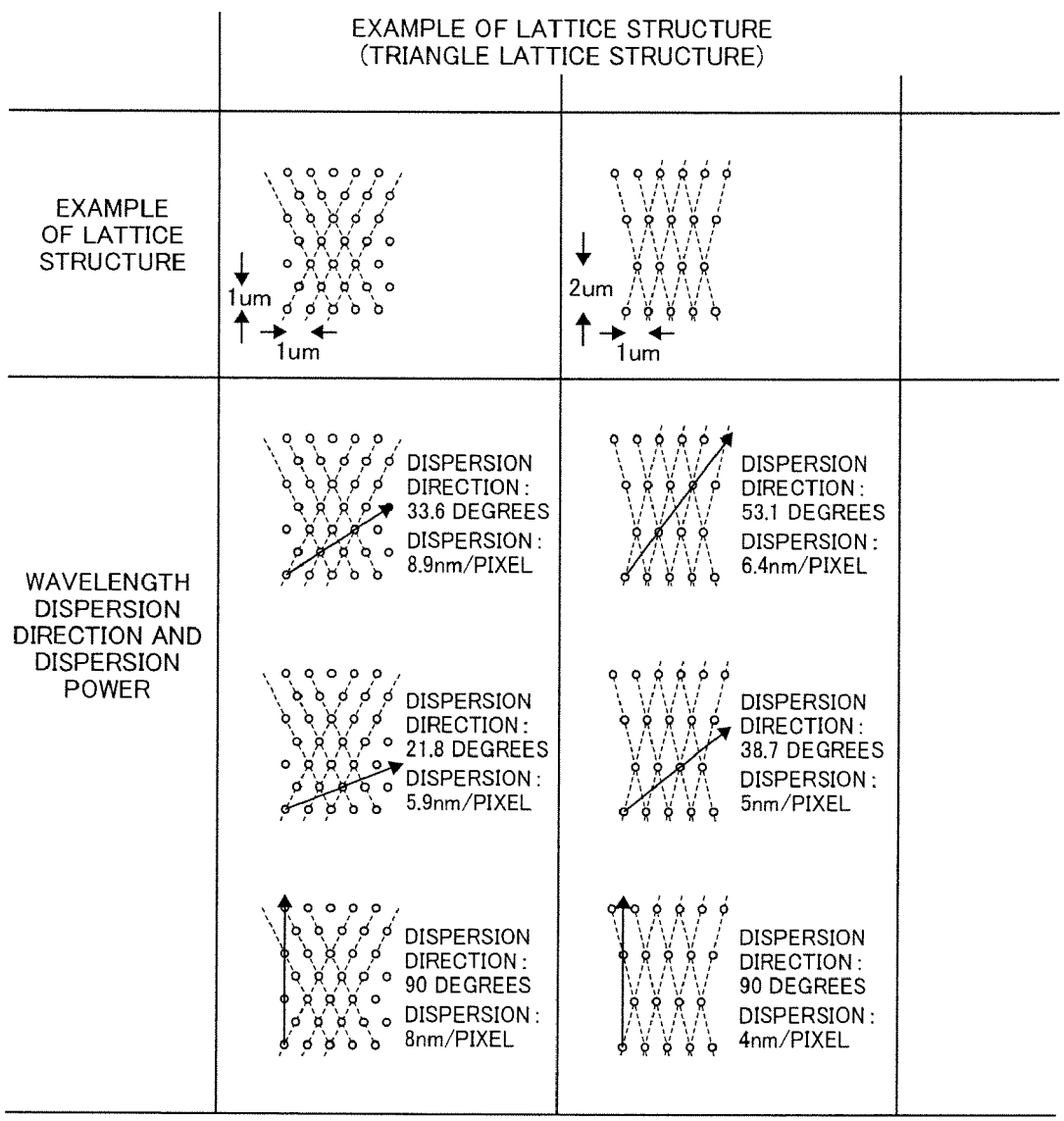
FIG. 6 is a conceptual diagram of lattice structures of a substrate and dispersion directions in a fourth embodiment.

FIG. 6 is a schematic diagram showing lattice structures of a further substrate and dispersion directions. Different points from the first to third embodiments will be mainly described below.

FIG. 6 illustrates the dispersion direction at each lattice point and a wavelength dispersion bandwidth per pixel of the CCD in the case of a triangle lattice structure. The conditions for this are the same as those of the third embodiment. In this embodiment, the wavelength dispersion direction is set to the direction toward a lattice point other than the closest lattice point, whereby the wavelength bandwidth per pixel can be enlarged without overlapping the fluorescence image from the set lattice point on fluorescence images from other lattice points. Thus, the intensity and wavelength of fluorescence can be detected with high accuracy.

Fifth Embodiment

Figure 7:
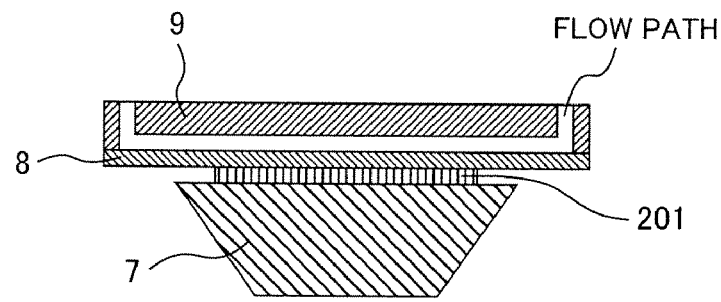
FIG. 7 is a configuration diagram of a bonding portion with a prism in a fifth embodiment.

FIG. 7 shows another structure of a bonding portion between the substrate and a prism for evanescence irradiation. Different points from the first to fourth embodiments will be mainly described below.

In this embodiment, like the first embodiment, the substrate 8 is coupled to the quartz prism 7. They are bonded together via a transparent elastic material as a coupling material, for example, a PDMS resin 201 (refractive index=1.42, internal transmittance=0.966/2 mm in thickness). The PDMS resin has a refractive index similar to that of glass, and is transparent. The PDMS resin is sandwiched between the substrate and the prism by press to be optically bonded together. During measurement, the visual field for measurement can be moved by an XY stage with the prism.

Sixth Embodiment

Figure 8:
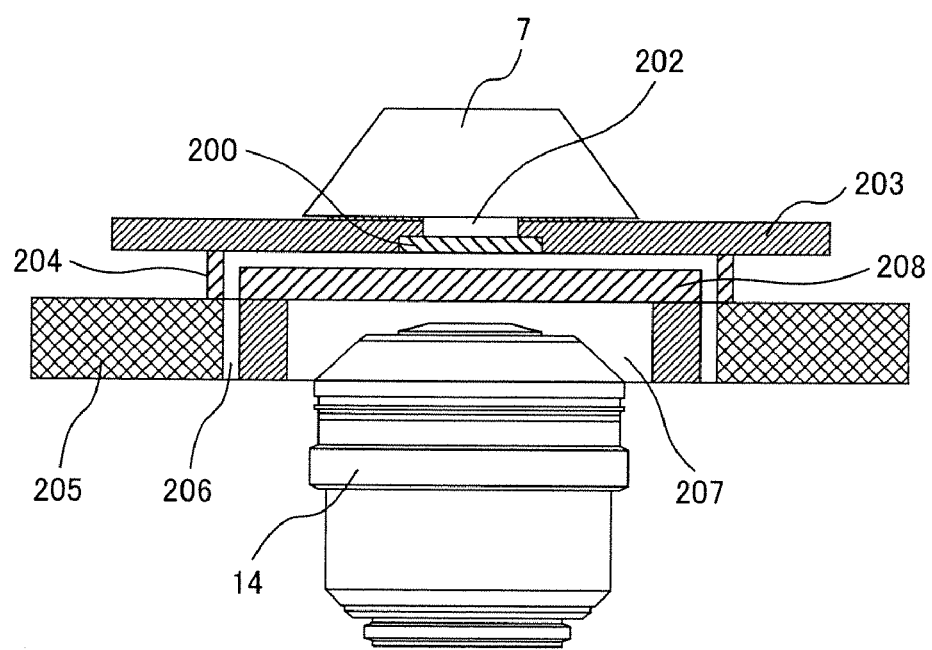
FIG. 8 is a configuration diagram of a bonding portion with a prism in a sixth embodiment.
Figure 9:
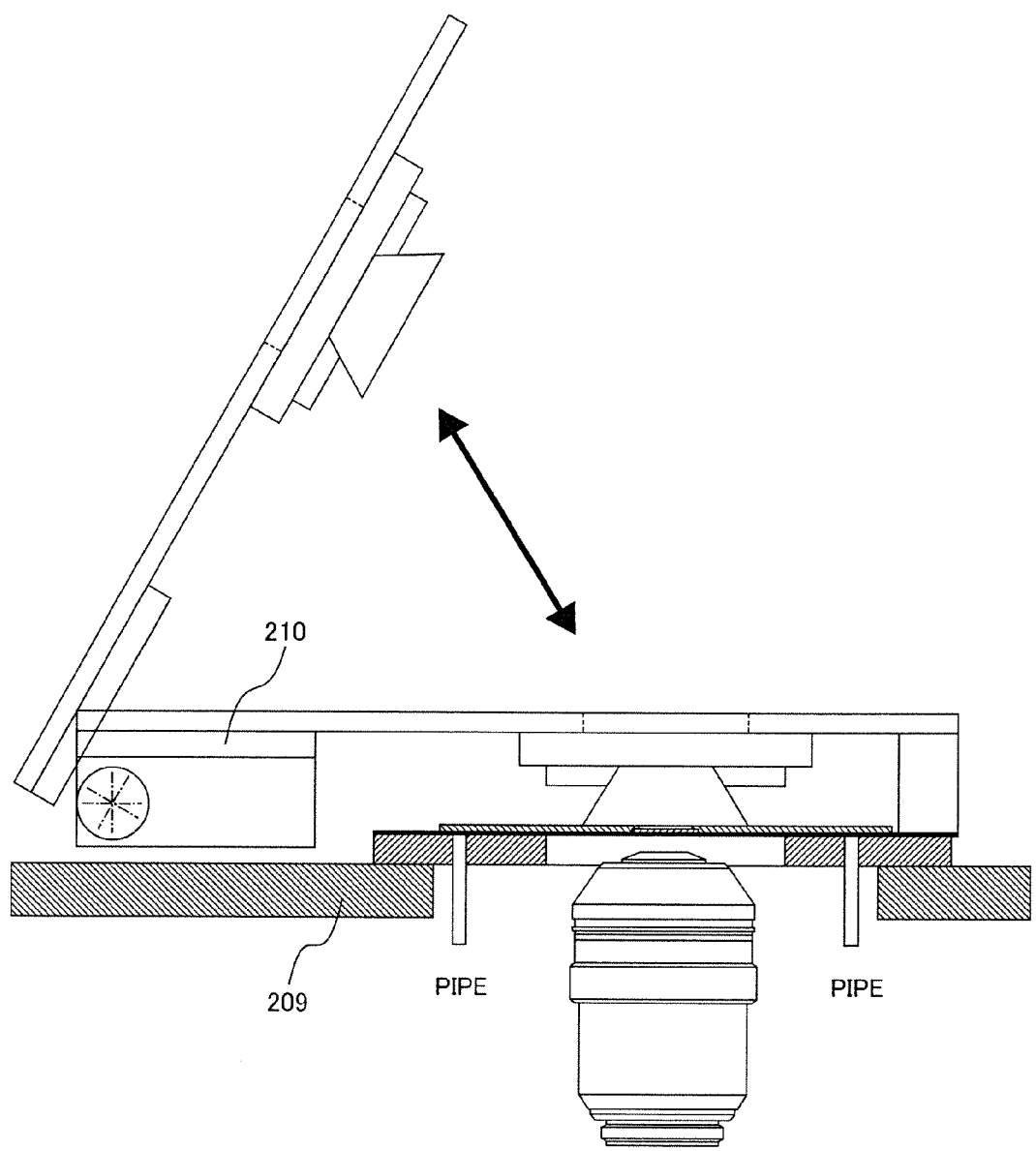
FIG. 9 is a configuration diagram of a prism holder in the sixth embodiment.

FIGS. 8 and 9 show another structure of a bonded portion between the substrate and a prism for evanescence irradiation. Different points from the first to fifth embodiments will be mainly described below.

In this embodiment, a measurement substrate 200 is embedded and fixed into a dedicated holder 203. Under, the holder, a flow chamber 204 is fixed. The flow chamber 204 is formed of PDMS, and bonded to the holder 203, which can allow a reagent, washing liquid, or the like to flow through the reaction region of the measurement substrate 200. This is brought into contact with a substrate holder 205 fixed to an XY stage 209 (shown in FIG. 9). A flow path 208 of the flow chamber 204 is aligned with a through hole 206. The through hole 206 is coupled to an external flow system. The substrate holder 205 has a large opening 207 at its center, and the condenser lens 14 and the measurement substrate 200 can get close to each other to thereby collect the fluorescences with high efficiency.

A matching oil is held in a recess 202 within the holder 203 at the backside (upper side shown in the figure) of the measurement substrate 200, and the prism 7 is disposed. The recess 202 is filled up with a PDMS resin instead of the matching oil, and may be matched.

The prism 7 is fixed to the prism holder 210, and has a detachable function from the substrate. In the case of evanescence irradiation, the prism 7 is bonded to the substrate.

The prism is made of acrylic or the like, and a member including a prism and a substrate which are integrally fixed to each other can be used.

Seventh Embodiment

Another example of a reaction substance will be described below. Different points from the first to seventh embodiments will be mainly described below.

Figure 10:
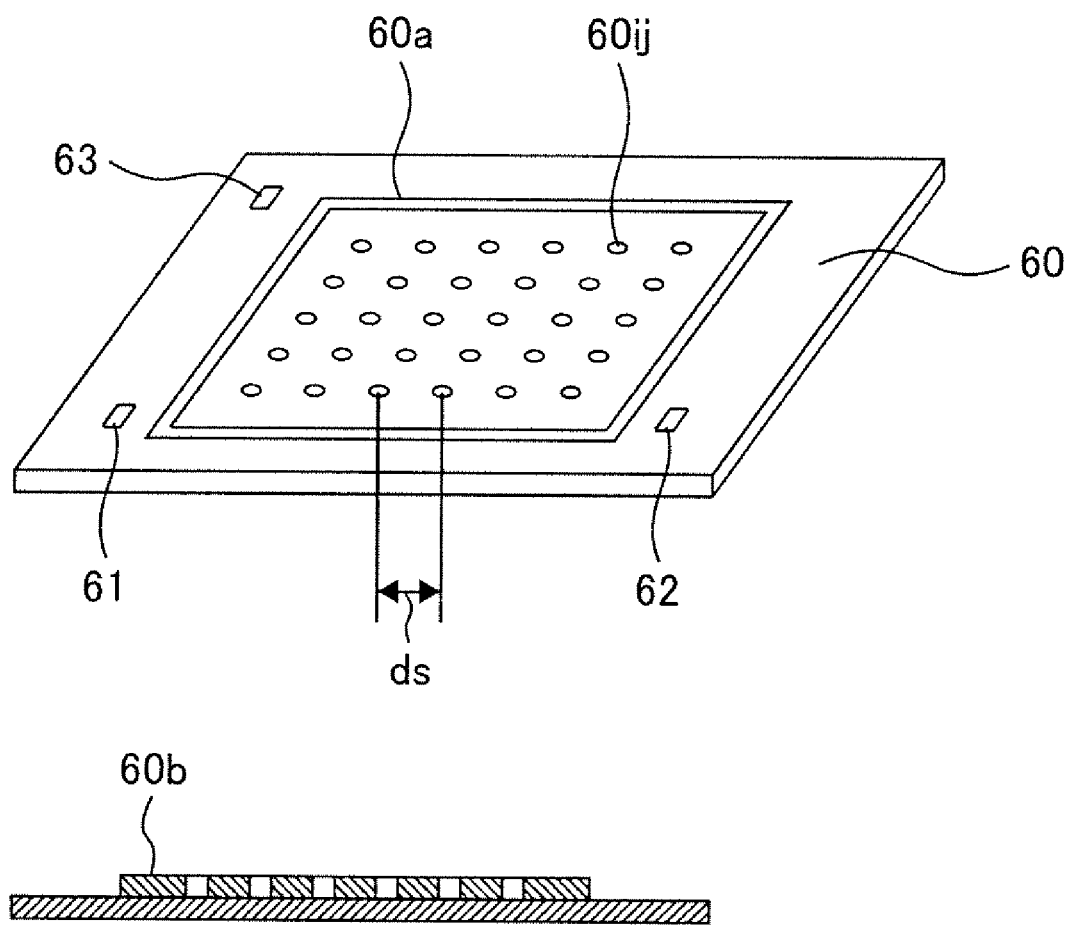
FIG. 10 is a configuration diagram of a substrate in a seventh embodiment.

FIG. 10 illustrates the structure of a reaction substrate of this embodiment. A substrate 60 has a reaction region 60*a*. Regions 60*ij* with the DNA immobilized thereon are formed in the reaction region 60*a*. Each region 60*ij* has its surroundings covered with an optical opaque mask 60*b*. As materials for the mask, metal, such as aluminum or chrome, and silicon carbide or the like can be used, and the material is formed thinly by deposition or the like. Each reaction region 60*ij* has a diameter of 100 nm or less. Methods for forming this opening inside the mask 60*b* includes vapor deposition (depositing while disposing an appropriate mask between a vapor deposition source and a substrate) by a projection method, and direct writing or the like by an electron-beam lithography or a photolithography. Alternatively, dry etching or wet etching may be used.

In a substrate made of a metal thin film having fine openings, biomolecules are immobilized into the openings. In this case, by detecting a Raman scattered light of a specimen solution around biomolecules and a photoluminescence and light scattering of the metal structure near the biomolecules, the spatial position of the metal structure can be detected and used as a reference marker for the position.

The metal structure may be formed in the opening.

This embodiment also obtains the same effects as those of the first embodiment. The area other than the reaction regions 60$ij$ is covered with the mask, which can reduce unnecessary stray light and fluorescence. Thus, the measurement of the fluorescence of interest can be measured with higher sensitivity.

Industrial Applicability

The present invention can be applied to a DNA sequencer using an elongation reaction, a total reflection fluorescence type DNA microarray reader, and the like.

Reference Signs List
  5, 104$b$ mirror prism
  8, 60 substrate
  8$a$, 60$a$ reaction region
  8$ij$ region with DNA immobilized thereon (dx and dy: size of spacing between regions 8$ij$)
  9 flow chamber
  10 waste liquid tube
  11 waste liquid container
  12 inlet
  13 fluorescence
  14 condenser lens (objective lens)
  15 filter unit
  16 a unit or a lens tube for observation of transmitted light
  17$a$, 17$b$ wavelength dispersion prism
  18$a$, 18$b$ imaging lens
  19$a$, 19$b$ two-dimensional sensor camera
  20$a$, 20$b$ two-dimensional sensor camera controller
  21 control PC
  22, 24 monitor
  23 TV camera
  25 dispensing unit
  26 dispensing nozzle
  27 reagent storage unit
  27$a$ specimen solution container
  27$b$, 27$c$, 27$d$, 27$e$ dNTP derivative solution container
  27$f$ washing liquid container
  28 chip box
  29 automatic focusing device
  30, 31, 61, 62, 63 positioning marker
  32, 103, 104$a$ dichroic mirror
  60$b$ mask
  60$ij$ reaction region with DNA immobilized thereon
  100, 101$a$, 101$b$, 101$c$, 101$d$ laser light source
  102$a$, 102$b$, 102$c$, 102$d$ λ/4 wave plate
  200 measurement substrate
  201 PDMS resin
  202 recess
  203 holder
  204 flow chamber
  205 substrate holder
  206 through hole
  207 opening
  208 flow path
  209 XY stage
  210 prism holder

The invention claimed is:

1. A fluorescence analyzing device, comprising a substrate where a biologically-related molecule is immobilized, the fluorescence analyzing device being adapted to irradiate the substrate with light for measurement of fluorescence, to disperse a generated fluorescence, and to measure the dispersed fluorescence by a two-dimensional sensor,
  wherein a plurality of regions where the biologically-related molecules can be immobilized are provided in positions of lattice points of a lattice structure at the substrate, and
  wherein a fluorescence generated from a certain lattice point is wavelength-dispersed in a direction other than a direction toward the adjacent closest lattice point.

2. The fluorescence analyzing device according to claim 1, wherein the fluorescence generated from the certain lattice point is wavelength-dispersed in the direction at an angle of +10 to +170 degrees, or −10 to −170 degrees with respect to an angle from the lattice point toward the adjacent closest lattice point.

3. The fluorescence analyzing device according to claim 1, wherein the fluorescence generated from the certain lattice point is wavelength-dispersed in a direction toward an arbitrary lattice point which is the second or higher-order closest from the lattice point.

4. The fluorescence analyzing device according to claim 1, wherein the lattice structure is a two-dimensional longitudinal lattice structure.

5. The fluorescence analyzing device according to claim 1, wherein the lattice structure is a triangle lattice structure.

6. The fluorescence analyzing device according to claim 1, wherein a metal fine structure is provided in the position of the lattice point of the lattice structure.

7. The fluorescence analyzing device according to claim 6, wherein the metal fine structure includes fine particles made of gold, chrome, silver, or aluminum.

8. The fluorescence analyzing device according to claim 6, wherein the metal fine structure is a structure whose part has a fine protrusion.

9. The fluorescence analyzing device according to claim 6, wherein the metal fine structure is a metal structure having a size equal to or less than a wavelength of an excitation light.

10. The fluorescence analyzing device according to claim 6, wherein the biologically-related molecule is immobilized on a surface of the metal structure, or a bottom of the opening.

11. The fluorescence analyzing device according to claim 1, wherein the substrate is used which has a fine opening located in the position of the lattice point of the lattice structure, and which is formed of an optically opaque thin film.

12. The fluorescence analyzing device according to claim 11, wherein the biologically-related molecule is immobilized on a surface of the metal structure, or a bottom of the opening.

13. The fluorescence analyzing device according to claim 1, wherein a prism is optically bonded to the substrate, or a part of the substrate has a prism-like shape, and
  wherein light for measurement of fluorescence is applied to the substrate via the prism, so that the light is totally reflected by a surface of the substrate to thereby form an evanescent field.

14. The fluorescence analyzing device according to claim 1, wherein an optically transparent elastic material is sandwiched between the substrate and a prism, so that the substrate is optically bonded to the prism, and wherein light for measurement of fluorescence is totally reflected by a surface of the substrate to thereby form an evanescent field.

15. The fluorescence analyzing device according to claim 1, wherein a distance between the lattice points is in a range of 100 nm to 10000 nm.

16. The fluorescence analyzing device according to claim 1, wherein the region where the biologically-related molecule can be immobilized has a diameter of 100 nm or less.

17. The fluorescence analyzing device according to claim 1, wherein the fluorescence is dispersed at a wavelength in a range of 500 nm to 700 nm.

18. The fluorescence analyzing device according to claim 1, wherein the fluorescence is separated into components with at least two wavelength bands, which are individually wavelength-dispersed.

19. The fluorescence analyzing device according to claim 1, wherein the fluorescence is separated into components with at least two wavelength bands, which are individually wavelength-dispersed within a maximum bandwidth of 100 nm, and respectively detected by two two-dimensional sensors.

20. A method for analyzing fluorescence, comprising the steps of:
- irradiating a substrate where a biologically-related molecule is immobilized, with light for measurement of fluorescence;
- dispersing a generated fluorescence; and
- measuring the dispersed fluorescence by a two-dimensional sensor,
- wherein a plurality of regions where the biologically-related molecules can be immobilized are provided in positions of lattice points of a lattice structure at the substrate, and
- wherein a fluorescence generated from a certain lattice point is wavelength-dispersed in a direction other than a direction toward the adjacent closest lattice point.

* * * * *